United States Patent [19]

Griggs

[11] Patent Number: 4,641,640
[45] Date of Patent: Feb. 10, 1987

[54] COMPRESSION SCREW ASSEMBLY

[76] Inventor: Calvin Griggs, 1455 Shady Birch, Memphis, Tenn. 38116

[21] Appl. No.: 675,934

[22] Filed: Nov. 28, 1984

Related U.S. Application Data

[62] Division of Ser. No. 340,093, Jan. 18, 1982, Pat. No. 4,530,355.

[51] Int. Cl.$^4$ .............................................. A61F 5/04
[52] U.S. Cl. ............................ 128/92 YV; 128/92 YE
[58] Field of Search ......... 128/92 BB, 92 BA, 92 BC, 128/92 B, 92 R

[56] References Cited

U.S. PATENT DOCUMENTS

| | | | |
|---|---|---|---|
| 2,243,717 | 5/1941 | Moreia | 128/92 BB |
| 2,267,925 | 12/1941 | Johnston | 128/92 BB |
| 2,702,543 | 2/1955 | Pugh et al. | 128/92 BB |
| 3,094,120 | 6/1963 | Blosser | 128/92 BB |
| 3,103,926 | 9/1963 | Cochran et al. | 128/92 BB |
| 3,374,786 | 3/1968 | Callender, Jr. | 128/92 BB |
| 3,842,825 | 10/1974 | Wagner | 128/92 BB |
| 4,095,591 | 6/1978 | Graham, Jr. et al. | 128/92 BB |
| 4,432,358 | 2/1984 | Fixel | 128/92 BB |
| 4,441,492 | 4/1984 | Rydell et al. | 128/92 BA |
| 4,530,355 | 7/1985 | Griggs | 128/92 BB |

Primary Examiner—Robert Peshock
Assistant Examiner—C. W. Shedd

[57] ABSTRACT

A compression screw assembly for applying compression to a fractured bone includes a lag screw, a compression plate including a hollow barrel member adapted to receive the lag screw in at least one fixed orientation, a wrench assembly adapted to releasably engage the lag screw in axial alignment therewith, and apparatus having surface contours complimentary with the outer surface of the lag screw and inner surface of the barrel member for being optionally insertable into the barrel member to prevent axial rotation of the lag screw with respect to the barrel member.

4 Claims, 20 Drawing Figures

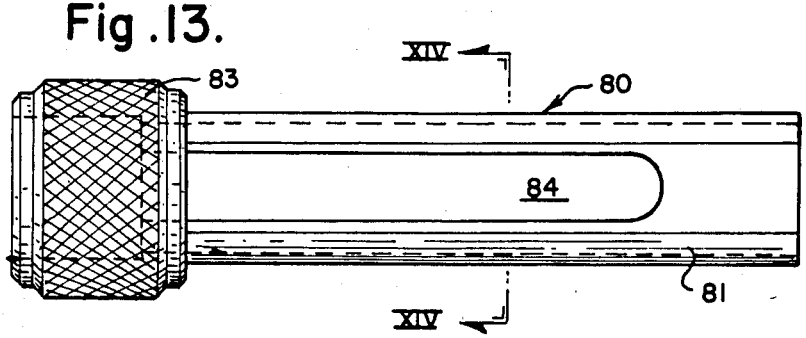
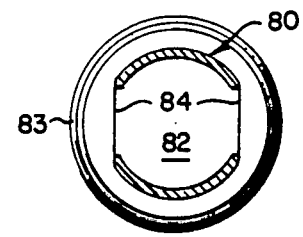
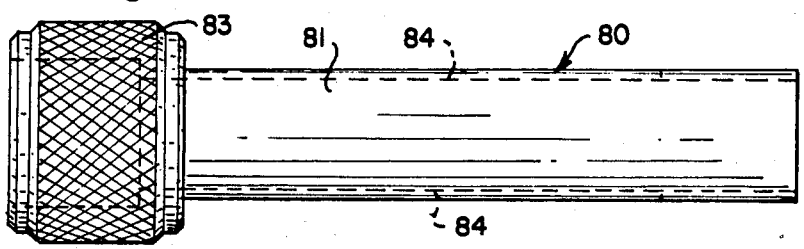
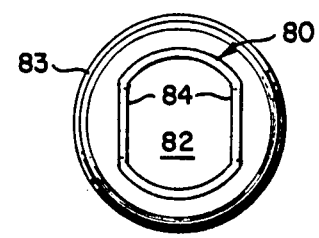
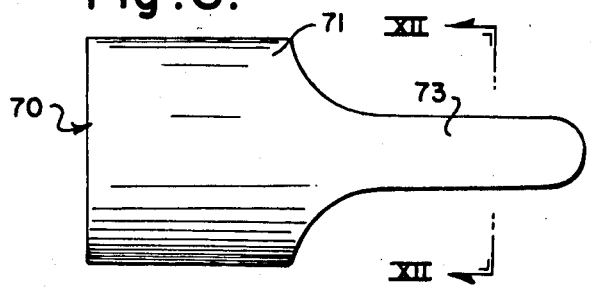
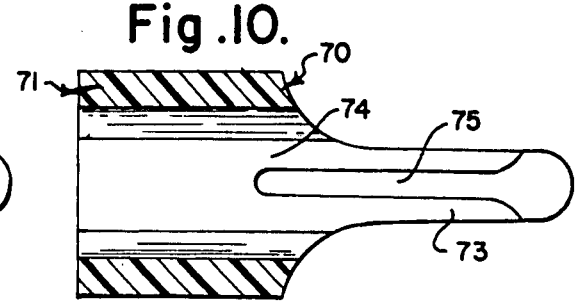
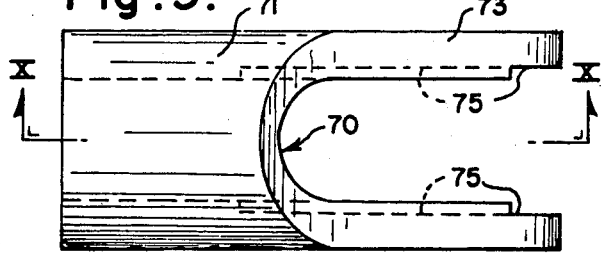
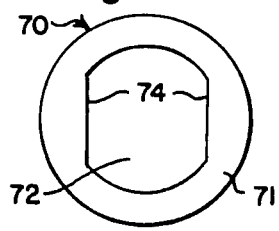
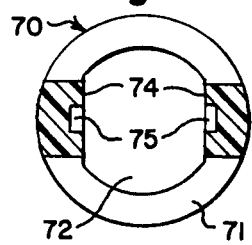
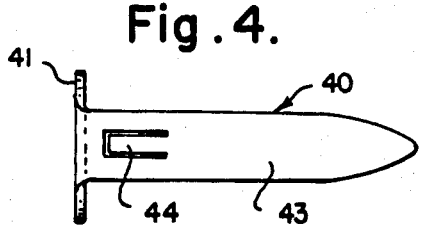
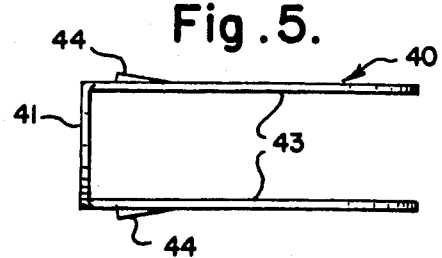
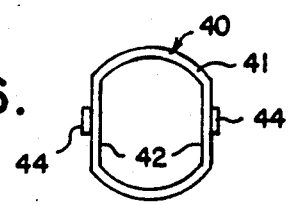
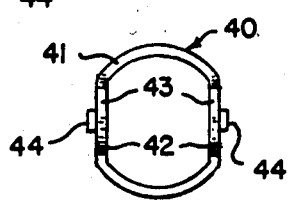

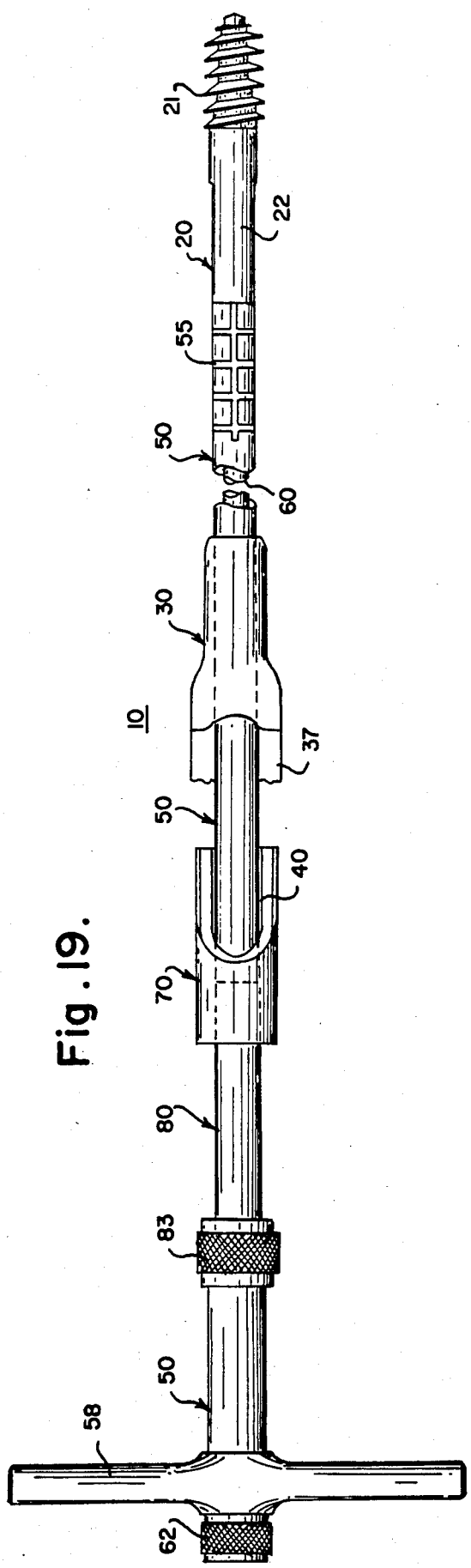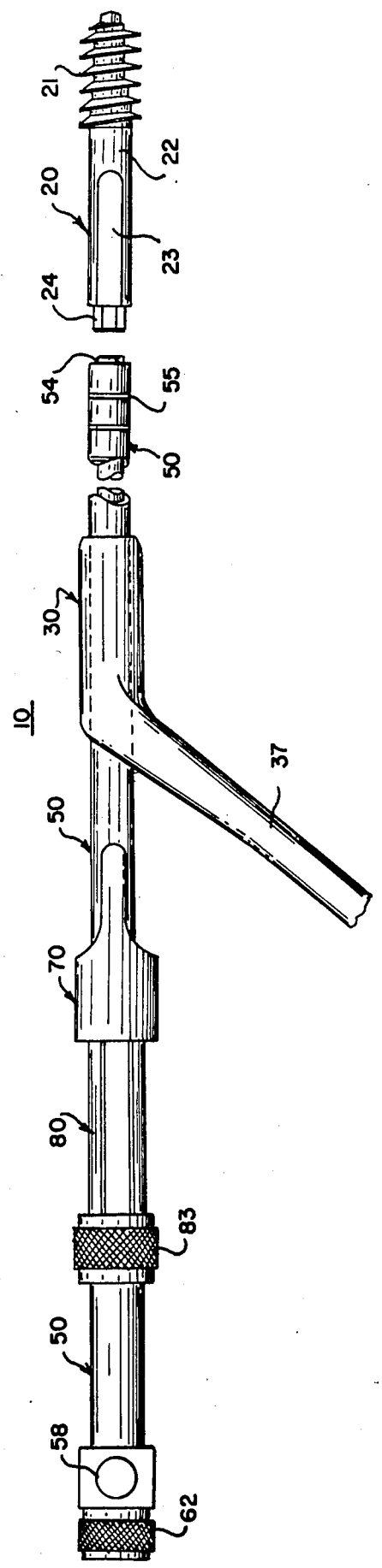
Fig. 19.
Fig. 20.

COMPRESSION SCREW ASSEMBLY

This is a divisional of co-pending application Ser. No. 340,093 filed on Jan. 18, 1982, now U.S. Pat. No. 4,530,355.

BACKGROUND OF THE INVENTION

1. Field of the Invention

The invention relates generally to a compression screw assembly for applying a compressive force to a fractured bone and more specifically to a compression screw system including a lag screw, compression plate and compression screw which can be assembled, aligned and installed so that the lag screw is non-rotatably secured to the compression plate at the option of the surgeon.

2. Description of the Prior Art

Workers in the art have devised various compression screw systems for applying compression to a fractured bone. Generally, the systems include a lag screw which extends from the shaft of the bone through the fracture and is anchored in the head of the bone, a compression plate which is adapted to extend over at least a portion of the head of the lag screw and which is anchored to the shaft of the bone and a compression screw which extends from the compression plate to the lag screw to permit the application of a compressive force between the lag screw and the compression plate.

It is often desirable to assure that the lag screw is non-rotatably secured to the compression plate. Generally this is accomplished in a keyed system by providing the lag screw with a longitudinally directed keyway, and by providing the portion of the hollow barrel of the compression plate that extends over the head of the lag screw with a corresponding longitudinally directed key. The problem with these systems is that it is difficult to insert the compression plate over the lag screw so that the key and keyway are aligned properly because the lag screw is driven completely into the bone before the compression plate is inserted.

One method for alleviating the problem of aligning the lag screw and compression plate is to provide an extension attached to the head of the lag screw to permit the lag screw to be aligned with the plate barrel more easily. A second method is to recess the key of the barrel member away from the front end of the barrel member so that the alignment occurs in two distinct steps: first, the aperture of the barrel member of the compression plate is aligned with the lag screw; and second, the key of the barrel member is aligned with the keyway of the lag screw. In a still further method as shown in U.S. Pat. No. 4,095,591, a barrel guide means having an extension member extending outward of the bone and having a cross section similar to that of the lag screw is used so that the barrel member of the compression plate is aligned on the extension member before it is inserted into the fractured bone.

A major disadvantage of the compression screw systems mentioned above is that the surgeon must determine before the insertion of the lag screw whether to use a keyed system or a non-keyed system. If a keyed system is to be used, the lag screw and compression plate must have the keyway and key, respectively. If a non-keyed system is to be used, the lag screw must be able to freely rotate within the barrel of the compression plate.

Accordingly, here exists a need for a compression screw assembly wherein the parts are properly aligned and installed and thereafter the lag screw may be non-rotatably secured to the compression plate at the option of the surgeon.

SUMMARY OF THE INVENTION

The present invention provides a compression screw system including a lag screw, compression plate, compression screw and wrench assembly whereby the lag screw can be non-rotatably secured to the compression plate at the option of the surgeon. In addition, the compression screw system can be assembled and properly aligned prior to the insertion of the lag screw and compression plate into the bone.

The compression plate includes a hollow barrel member adapted to receive one end of the lag screw in at least one fixed orientation. The barrel member and lag screw are adapted to receive a member, preferably a clip, therebetween which, when inserted between the inner surface of the barrel member and the lag screw, prevents axial rotation of the lag screw with respect to the barrel member of the compression plate as in a keyed system. If the clip is not inserted within the barrel member of the compression plate the lag screw is able to freely rotate with respect to the compression plate as in a keyless system. The clip may be inserted within the barrel member of the compression plate at the option of the surgeon, and the decision of the surgeon may be reserved until the time when the clip is to be inserted.

Preferably, the wrench assembly includes a wrench for releasably engaging the lag screw into the bone, a member for holding the clip in place on the wrench prior to the insertion of the clip into the barrel member of the compression plate, a member for pushing the clip from the holding member into the barrel member of the compression plate between the inner surface of the barrel member and the lag screw, and a stabilizing rod for stabilizing the wrench assembly during the insertion of the lag screw and compression plate into the fractured bone.

In the preferred embodiment, the contour of the outer surfaces of the lag screw and the wrench are identical and are adapted so that the compression plate, clip, holding member and pushing member which have identical corresponding inner surface contours, can be inserted over the wrench and lag screw in the proper axial alignment. Preferably, the configurations are substantially round and include two flat portions, spaced 180° apart. Thus, the compression screw system can be aligned properly by aligning the flat portions of each member of the assembly.

BRIEF DESCRIPTION OF THE DRAWINGS

FIG. 4 is a top plan view of the clip of the assembly shown in FIG. 1;

FIG. 5 is a side elevational view of the clip shown in FIG. 4;

FIG. 6 is a front elevational view of the clip shown in FIG. 4;

FIG. 7 is a rear elevational view of the clip shown in FIG. 4;

FIG. 8 is a top plan view of the clip holder for the clip shown in FIG. 4;

FIG. 9 is a side elevational view of the clip holder shown in FIG. 8;

FIG. 10 is a sectional view of the clip holder shown in FIG. 9 taken along the line X—X;

FIG. 11 is a rear elevational view of the clip holder shown in FIG. 8;

FIG. 12 is a cross-sectional view of the clip holder shown in FIG. 8 taken along the line XII—XII;

FIG. 13 is a side elevational view of the clip pusher for the clip shown in FIG. 4;

FIG. 14 is a cross-sectional view of the clip pusher shown in FIG. 13 taken along the line XIV—XIV;

FIG. 15 is a top plan view of the clip pusher shown in FIG. 13;

FIG. 16 is a front elevational view of the clip pusher as shown in FIG. 13;

FIG. 19 is a top view, in partial cutaway, of the hip screw assembly prior to the installation of the hip screw; and FIG. 20 is a side view of the hip screw assembly shown in FIG. 19;

DETAILED DESCRIPTION OF THE PREFERRED EMBODIMENTS

Figure 1:
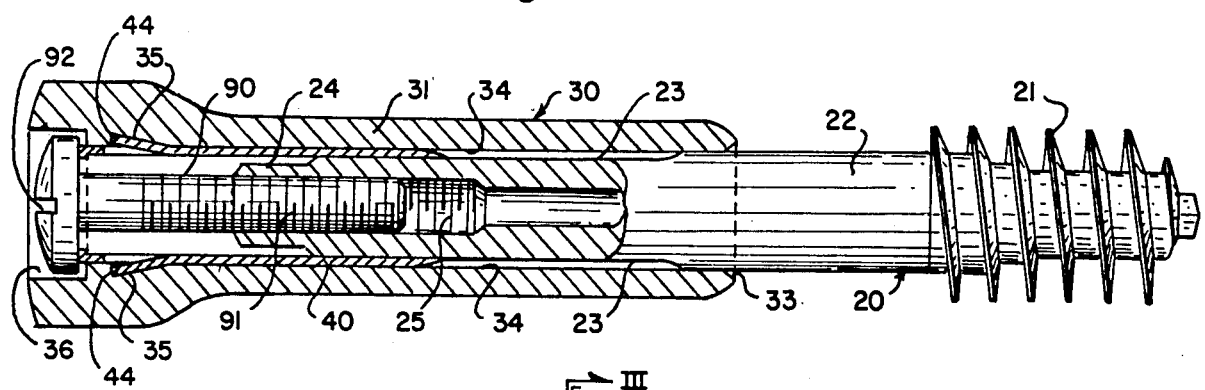
FIG. 1 is a sectional view of the hip screw assembly as installed in a bone according to the present invention.
Figure 2:
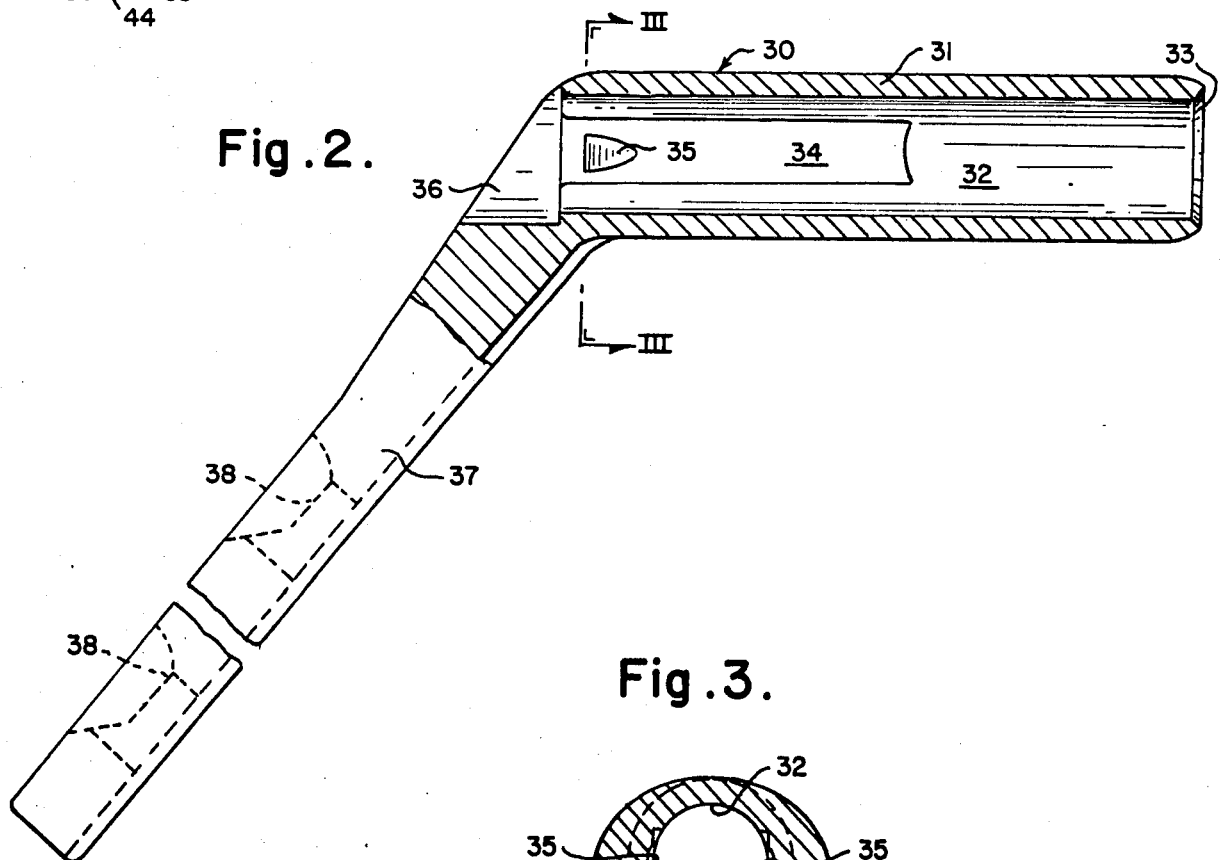
FIG. 2 is a sectional view of the compression plate of the assembly shown in FIG. 1.
Figure 3:
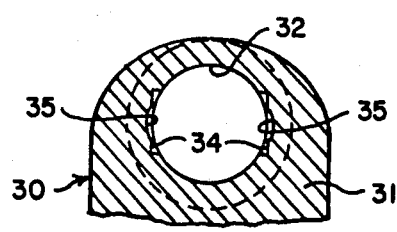
FIG. 3 is a cross-sectional view of the compression plate shown in FIG. 2 taken along the line III—III.

As shown in the Figures, compression screw assembly 10 consists of lag screw 20, compression plate 30, clip 40, wrench 50, stabilizing rod 60, clip holder 70, clip pusher 80 and compression screw 90.

Referring to FIGS. 1, 19 and 20, lag screw 20 includes a screw head 21 formed at one end of an elongated shaft 22 adapted to be installed into the shaft of the fractured bone, through the fracture, and anchored in the head of the fractured bone. Shaft 22 has a substantially circular cross section with flat portions 23 formed on either side of its outer edge. The second end of lag screw 20 includes drive portion 24. The cross section of drive portion 24 is smaller than that of the remainder of lag screw 20, and is preferably of a modified hexagonal configuration having six sides, one pair of opposing sides being of a different length than the other four sides. Drive portion 23 is adapted to fit within bore 54 of wrench 50 when compression screw assembly 10 is assembled. Lag screw 20 has a bore extending therethrough so that lag screw 20 can be inserted over a guide wire. The bore of lag screw 20 contains a threaded portion 25 so that compression screw 90 can be threaded therein. In addition, the threaded portion formed at the lower end of stabilizing rod 60 is inserted within threaded portion 25 when compression screw assembly 10 is assembled.

As shown in FIGS. 1, 2, 3, 19 and 20 compression plate 30 includes barrel member 31 having a bore 32 extending therethrough of a size that permits bore 32 to accept the second end of lag screw 20 through end 33 of compression plate 30. The surface of bore 32 of barrel member 31 includes two flat portions 34 corresponding to flat portions 23 formed on the outer surface of lag screw 20 to permit insertion of clip 40 between flat portions 34 of barrel member 31 and flat portions 23 formed on the outer surface of lag screw 20. Each flat portion 34 includes an indentation 35 adapted to receive a tang 44 of clip 40. End 36 of bore 32 is adapted to receive compression screw 90 therein. Compression plate 30 also includes a member 37 for enabling compression plate 30 to be anchored to the shaft of the bone. Member 37 contains a plurality of holes 38 for the insertion of bone screws therethrough in order to anchor compression plate 30 to the shaft of the bone.

Clip 40, illustrated in FIGS. 1, 4 through 7, and 17 through 19, includes ring 41 having two flat portions 42. The inner surface of ring 41 is of a size that permits ring 41 to accept the second end of lag screw 20 and wrench 50; the outer edge of ring 41 is of a size adapted to permit insertion of clip 40 into bore 32 of barrel member 31 and bore 72 of clip holder 70 that clip 40 can be inserted within bore 32 of barrel member 31 between the outer edge of lag screw 20 and the inner edge of barrel member 31. Two elongated members 43 extend perpendicularly from flat portions 42 of rings 41. Members 43 include tangs 44 which are adpted to be received by indentations 35 formed in the inner surface of barrel 31 of compression plate 30 and grooves 75 of clip holder 70.

Figure 17:
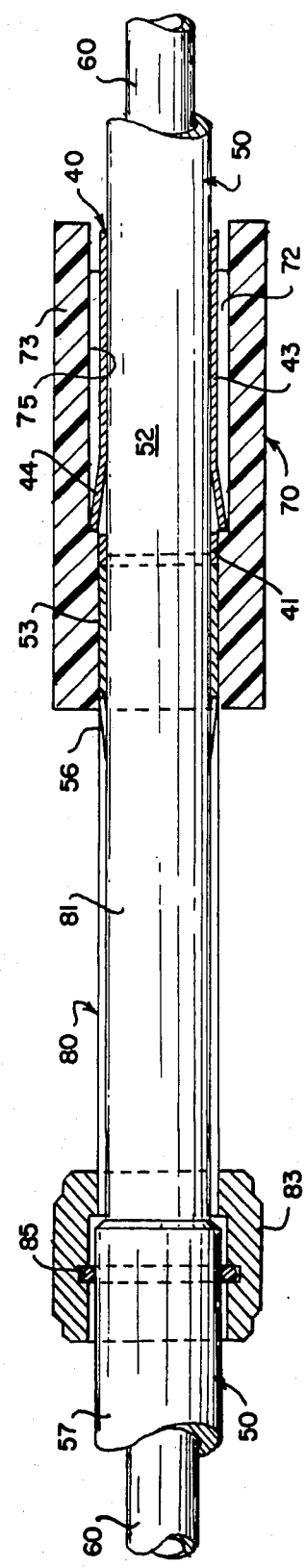
FIG. 17 is a top sectional view of the shaft assembly showing the clip pusher, clip holder and clip assembled for installation.
Figure 18:
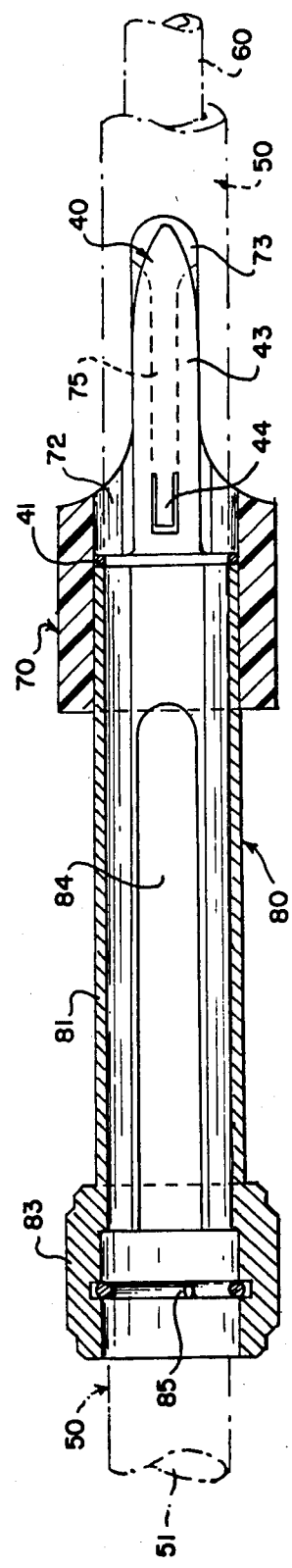
FIG. 18 side sectional view of the shaft assembly as shown in FIG. 17.

Referring to FIGS. 17 through 20, wrench 50 includes bore 51 adapted to receive stabilizing rod 60. As shown in FIG. 17, the shaft of wrench 50 includes a first portion or lower shaft 52 and a second portion or upper shaft 57. Lower shaft 52 has a smaller circumference than upper shaft 57. The lower shaft 52 of wrench 50 has an outer surface cross-section adapted to match that of lag screw 20 and includes flat portions 53 which correspond to flat portions 23 of lag screw 20. The end of lower shaft 52 contains drive portion 54, the inner surface of which has a shape corresponding to drive portion 24 of lag screw 20 and is adapted to accept drive portion 24. Depth markings 55, formed in the non-flat portions of wrench 50, are used as assembly 10 is installed in a bone shaft. Lower shaft 52 includes stops 56 formed on its outer surface at its upper end. Stops 56 are protruding portions of lower shaft 52 which are used to prevent premature separation of clip 40 and clip holder 70. The outer edge of upper shaft 57 of wrench 50 is of a larger circumference than that of lower shaft 52 and does not include any flat portions. Upper shaft 57 ends in a T-shaped handle 58. The plane passing through both arms of handle 58 is perpendicular to the plane passing through flat portions 53.

As illustrated in FIGS. 17 through 20, stabilizing rod 60 is inserted through bore 51 of wrench 50. Stabilizing rod 60 is cannulated so that compression screw system 10 can be threaded over a guide wire to aid in directing the insertion of lag screw 20 into the bone. Stabilizing rod 60 includes a threaded portion at its lower end which can be threaded within portion 25 of lag screw 20. Stabilizing rod 60 also includes knurled end 62.

Clip holder 70, shown in FIGS. 8 through 12 and 17 through 20, includes an upper barrel portion 71 having a bore 72 extending therethrough and two elongated members 73 extending therefrom. The inner surface of clip holder 70 includes flat portions 74. The inner surface of clip holder 70 is adapted to receive clip 40 and includes grooves 75 that receive tangs 44 of clip 40.

Referring to FIGS. 13 through 20, clip pusher 80 includes barrel portion 81 having a bore 82 extending therethrough, and knurled end 83. Barrel portion 81 includes slots 84 formed in either side. As clip pusher 80 is slid along wrench 50, the lower end of each slot 84 engages a stop 56 to prevent further movement of clip pusher 80 along wrench 50. Ring 85 is disposed within knurled end 83 to frictionally engage upper shaft 57 of wrench 50 as clip pusher 80 is slid along wrench 50. The outer surface of clip pusher 80 includes flat portions 86 at its lower end corresponding to flat portions 74 of clip holder 70.

Compression screw 90, shown in FIG. 1, includes threaded shaft 91 which can be threaded into portion 25 of lag screw 20, and includes slot drive 92. Other well known drives, such as the hex drive, may be used.

In order to assemble compression screw assembly 10, clip pusher 80 is mounted, knurled end 83 first, over the lower shaft 52 of wrench 50 so that flat portions 53 of wrench 50 are aligned with slots 84 of clip pusher 80. Clip pusher 80 is slid along shaft 52 of wrench 50 until slots 84 engage stops 56 of wrench 50 and ring 85 engages upper shaft 57 of wrench 50. Clip 40 then is inserted within bore 72 of clip holder 70 so that flat portions 42 of clip 40 are aligned with flat portions 74 of clip holder 70 and tangs 44 of clip 40 are disposed within grooves 75 of clip holder 70. Elongated members 43 of clip 40 are disposed under elongated members 73 of clip holder 70. Clip holder 70, now containing clip 40, is mounted, barrel portion 71 first, over lower shaft 52 of wrench 50 until clip holder 70 engages clip pusher 80.

Once clip 40, clip pusher 80 and clip holder 70 are in place, compression plate 30 is slid end 36 first, over lower shaft 52 of wrench 50. Wrench stabilizing rod 60 is inserted within bore 51 of wrench 50. The threaded portion of stabilizing rod 60 is threaded within portion 25 of lag screw 20 and drive portion 24 of lag screw 20 is inserted within corresponding drive portion 54 of wrench 50.

To use the compression screw system of the present invention, the surgeon must first insert a guide wire in to the fractured bone, and then use a reamer to ream out the root diameter corresponding to the size of lag screw 20 and the opening for the outside diameter of the barrel member 31 of compression plate 30.

Because stabilizing rod 60 is cannulated, compression screw assembly 10 can be inserted over the guide wire. Lag screw 20 is then threaded partway into the bone by turning handle 58 of wrench 50. Compression plate 30 is slid forward over insertion wrench 50 and over shaft 22 of lag screw 20 until compression plate 20 is flush against the bone. Lag screw 20 is then threaded fully into the bone to the proper depth as indicated by depth markings 55 on wrench 50.

If lag screw 20 and compression plate 30 are to be inserted so that lag screw 20 is non-rotatably secured to compression plate 30, clip pusher 80 with clip holder 70 and clip 40 attached is pushed forward until clip holder 70 touches and centers on compression plate 30, then pushed again, more firmly, to slide clip 40 from within clip holder 70 and into barrel member 31 of compression plate 30 so that tangs 44 of clip 40 become disposed within indentations 35 of barrel member 31. Once clip 40 is in place, clip pusher 80 and clip holder 70 are slipped back down insertion wrench 50. Stabilizing rod 60 is unthreaded from lag screw 20 and wrench 50 and stabilizer rod 60 are removed.

Regardless of whether clip 40 is inserted, compression screw 90 may be inserted through barrel 31 of compression plate 30 and threaded into threaded portion 25 of lag screw 20 to obtain a tight compression between lag screw 20 and compression plate 30. Once the desired amount of compression has been achieved, compression screw 90 may be removed or left in place at the option of the surgeon.

Finally, compression plate 30 is anchored to the bone by inserting bone screws through apertures 38 of member 37 and into the bone.

What is claimed is:

1. A lag screw for a compression screw assembly comprising:
   an engaging means formed thereon for coacting with a second complementary engaging means formed on the interior surface of a hollow barrel member of a compression plate so that said lag screw is adapted to be received into the hollow barrel member in at least one fixed orientation, said engaging means and said second complementary engaging means being proportioned to accept therebetween a third complementary engaging means of a means for being optionally insertable into the barrel member in order to selectively prevent axial rotation of said lag screw with respect to the barrel member; and
   a means for coacting with a wrench assembly so that said lag screw can be releasably engaged by the wrench assembly in axial alignment therewith.

2. A lag screw as recited in claim 1 wherein said engaging means are opposing flat portions on said lag screw, said second complementary engaging means are opposing flat portions on the interior surface of the hollow barrel member and said third complementary engaging means are opposing flat portions on the optionally insertable means to prevent axial rotation.

3. A lag screw as recited in claim 1 wherein said coacting means is a drive portion contoured for insertion within the bore of the wrench assembly so that the compression screw assembly can be assembled and axialy aligned prior to the insertion of said lag screw into bone.

4. A lag screw for use within the hollow barrel portion of the plate of a compression screw assembly, comprising:
   an elongated body member; and
   a first engaging surface formed on said body member and adapted for confronting alignment with a second engaging surface formed on the interior of said barrel;
   said first and second engaging surfaces being contoured relative to each other to receive therebetween an optionally insertable means having surface contours complementary with said first and second engaging surfaces to selectively prevent axial rotation of said body member with respect to said hollow barrel of said plate.

* * * * *

UNITED STATES PATENT AND TRADEMARK OFFICE
CERTIFICATE OF CORRECTION

PATENT NO. : 4,641,640

DATED : February 10, 1987

INVENTOR(S) : Calvin Griggs

It is certified that error appears in the above—identified patent and that said Letters Patent is hereby corrected as shown below:

Col. 2, line 1, delete "here" and substitute therefor --there--.

Col. 3, line 48, delete "23" and substitute therefor --24--.

Col. 4, line 18, delete "rings" and substitute therefor --ring--.

Signed and Sealed this

Thirteenth Day of October, 1987

Attest:

DONALD J. QUIGG

*Attesting Officer*  *Commissioner of Patents and Trademarks*